(12) United States Patent
Schachar

(10) Patent No.: US 8,663,205 B2
(45) Date of Patent: Mar. 4, 2014

(54) LASER PROCEDURE FOR TREATMENT OF PRESBYOPIA AND OTHER EYE DISORDERS

(75) Inventor: Ronald A. Schachar, Dallas, TX (US)

(73) Assignee: Refocus Ocular, Inc., Dallas, TX (US)

( * ) Notice: Subject to any disclaimer, the term of this patent is extended or adjusted under 35 U.S.C. 154(b) by 1926 days.

(21) Appl. No.: 11/322,728

(22) Filed: Dec. 30, 2005
(Under 37 CFR 1.47)

(65) Prior Publication Data

US 2006/0106457 A1 May 18, 2006

Related U.S. Application Data

(60) Continuation of application No. 09/556,143, filed on Apr. 21, 2000, now abandoned, which is a continuation of application No. 09/032,830, filed on Mar. 2, 1998, now Pat. No. 6,197,056, which is a continuation-in-part of application No. 08/462,649, filed on Jun. 5, 1995, now Pat. No. 5,722,952, which is a division of application No. 08/139,756, filed on Oct. 22, 1993, now Pat. No. 5,489,299, which is a division of application No. 07/913,486, filed on Jul. 15, 1992, now Pat. No. 5,354,331.

(51) Int. Cl.
*A61F 9/008* (2006.01)

(52) U.S. Cl.
USPC .............................. 606/4; 128/898

(58) Field of Classification Search
USPC ............................. 606/3–6, 10–17
See application file for complete search history.

(56) References Cited

U.S. PATENT DOCUMENTS

| | | |
|---|---|---|
| 2,952,023 A | 9/1960 | Rosen |
| 3,064,643 A | 11/1962 | Dixon |
| 3,454,966 A | 7/1969 | Rosen |
| 3,884,236 A | 5/1975 | Krasnov |
| 4,174,389 A | 11/1979 | Cope |
| 4,391,275 A | 7/1983 | Fankhauser et al. |
| 4,549,529 A | 10/1985 | White |
| 4,603,697 A | 8/1986 | Kamerling |
| 4,782,820 A | 11/1988 | Woods |
| 4,839,342 A | 6/1989 | Kaswan |

(Continued)

FOREIGN PATENT DOCUMENTS

| | | |
|---|---|---|
| SU | 1597188 | 10/1990 |
| SU | 1639647 | 4/1991 |
| WO | WO 89/09034 | 10/1989 |

OTHER PUBLICATIONS

March et al; "Safety of High-Energy Neodymium:YAG Laser Pulses in YAG Sclerostomy"; Lasers in Surgery and Medicin; vol. 6; 1987; pp. 584-587.*

(Continued)

*Primary Examiner* — David Shay

(57) ABSTRACT

A segmented scleral expansion band adapted for implantation within or fastening to a segment of the sclera of an eye lying outside of and adjacent to the ciliary body of the eye, is formed from a number of arcuate segments, curved to match the curvature of the globe of the eye, and joined together at each end to form a complete scleral expansion band. The band is implanted in the sclera of the eye by forming circumferential tunnels, inserting the band segments through the tunnels, and joining the ends of the segments to form a complete scleral expansion band. The scleral expansion band is useful in treating presbyopia and other ocular disorders.

3 Claims, 5 Drawing Sheets

(56) References Cited

U.S. PATENT DOCUMENTS

| | | | |
|---|---|---|---|
| 4,923,699 A | 5/1990 | Kaufman |
| 4,966,452 A | 10/1990 | Shields et al. |
| 4,976,709 A | 12/1990 | Sand |
| 4,976,719 A | 12/1990 | Siepser |
| 5,025,811 A | 6/1991 | Dobrogowski et al. |
| 5,152,759 A | 10/1992 | Parel et al. |
| 5,152,760 A | 10/1992 | Latina |
| 5,163,419 A | 11/1992 | Goldman |
| 5,174,304 A | 12/1992 | Latina et al. |
| 5,181,922 A | 1/1993 | Blumenkanz et al. |
| 5,267,553 A | 12/1993 | Graether |
| 5,292,514 A | 3/1994 | Capecchi et al. |
| 5,300,114 A | 4/1994 | Gwon et al. |
| 5,300,144 A | 4/1994 | Adams |
| 5,312,394 A | 5/1994 | Beckman |
| 5,354,331 A | 10/1994 | Schachar |
| 5,372,595 A | 12/1994 | Gaasterland et al. |
| 5,465,737 A | 11/1995 | Schachar |
| 5,472,436 A | 12/1995 | Fremstad |
| 5,476,511 A | 12/1995 | Gwon et al. |
| 5,489,299 A | 2/1996 | Schachar |
| 5,503,165 A | 4/1996 | Schachar |
| 5,529,076 A | 6/1996 | Schachar |
| RE35,974 E | 12/1998 | Davenport et al. |
| 6,197,056 B1 | 3/2001 | Schachar |

OTHER PUBLICATIONS

Robert A. Moses (Ed.); "Adler's Physiology of the Eye, Clinical application"; The C. V. Mosby Company, St. Louis, MO; 1975 pp. 183, 190, 191, 232-234.*

Minoru Araki, "Tendency of the Fluctuation of the Tension of Ciliary Zonules Associated to Accommodation", pp. 58-61.

R. F. Fisher, "The Significance of the Shape of the Lens and Capsular Energy Changes in Accommodation", J. Physiol (1969), 201, pp. 21-47.

R. F. Fisher, "The Elastic Constants of the Human Lens", J. Physiol (1971), 212, pp. 147-180.

R. F. Fisher et al., "Presbyopia and the Water Content of the Human Crystalline Lens", J. Physiol (1973), 234, pp. 443-447.

R. F. Fisher, "Presbyopia and the Changes with Age in the Human Crystalline Lens", J. Physiol (1973), 228, pp. 765-779.

R. F. Fisher, "The Force of Contraction of the Human Ciliary Muscle During Accommodation", J. Physiol (1977), 270, pp. 51-74.

R. F. Fisher, "The Vitreous and Lens in Accommodation", Trans. Ophthal. Soc. U.K. (1982) 102, pp. 318-322.

"Is the Vitreous Necessary for Accommodation in Man?", British Journal of Ophthalmology, 1983, 67, pp. 206.

R. F. Fisher, "The Mechanics of Accommodation in Relation to Presbyopia", Eye (1988), 2, pp. 646-649.

George O. Waring III, "Refractive Keratotomy for myopia and astigmatism".

Leo Bores, M.D., "American Experience with Myopia Procedure of Fyodorov", pp. 175-181.

James Salz, MD, et al., "Radial Keratotomy in Fresh Human Cadaver Eyes" Ophthalmology, vol. 88, No. 8, Aug. 1981, pp. 742-746.

Michael R. Deitz, MD, et al., "Radial Keratotomy: An Overview of the Kansas City Study", pp. 467-478.

Hajime Suzuki, "Observations on the Intraocular Changes Associated with Accommodation: An Experimental Study Using Radiographic Technique", Exp. Eye Res. (1973) 17, pp. 119-128.

Spencer P. Thornton, "Anterior Ciliary Sclerotomy (ACS), A Procedure to Reverse Presbyopia", Surgery for Hyperopia and Presbyopia, 1997, pp. 33-36.

Communication pursuant to Article 94(3) EPC in connection with European Patent Application No. 05 077 198.9 dated May 20, 2008.

* cited by examiner

LASER PROCEDURE FOR TREATMENT OF PRESBYOPIA AND OTHER EYE DISORDERS

PRIORITY CLAIM

This application is a continuation of U.S. patent application Ser. No. 09/556,143 filed on Apr. 21, 2000 now abandoned, which is a continuation-in-part of U.S. patent application Ser. No. 09/032,830 filed on Mar. 2, 1998 (now U.S. Pat. No. 6,197,056), which is a continuation-in-part of U.S. patent application Ser. No. 08/462,649 filed on Jun. 5, 1995 (now U.S. Pat. No. 5,722,952), which is a divisional of U.S. patent application Ser. No. 08/139,756 filed on Oct. 22, 1993 (now U.S. Pat. No. 5,489,299), which is a divisional of U.S. patent application Ser. No. 07/913,486 filed on Jul. 15, 1992 (now U.S. Pat. No. 5,354,331).

TECHNICAL FIELD

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle.

BACKGROUND

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed collagenous fibers, the zonules, which are attached at their inner ends to the lens capsule and at their outer ends to the ciliary body, a muscular ring of tissue located just within the outer supporting structure of the eye, the sclera. The ciliary body is relaxed in the unaccommodated eye and therefore assumes its largest diameter. According to the classical theory of accommodation, originating with Helmholtz, the relatively large diameter of the ciliary body in this condition causes a tension on the zonules which in turn pull radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent of the posterior surface, is less than it would be in the absence of the tension. In this state the refractive power of the lens is relatively low and the eye is focused for clear vision of distant objects.

When the eye is intended to be focused on a near object, the muscles of the ciliary body contract. According to the classical theory, this contraction causes the ciliary body to move forward and inward, thereby relaxing the outward pull of the zonules on the equator of the lens capsule. This reduced zonular tension allows the elastic capsule of the lens to contract causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of loss of elasticity of the lens capsule and/or sclerosis of the lens with age. Consequently, even though the radial tension on the zonules is relaxed by contraction of the muscles of the ciliary body, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings have been used in ocular surgery for various purposes. Rings of flexible and/or elastic material, prepared in situ by fastening the ends of strips of the material around the generally posterior portion of the globe have been used to compress the sclera in certain posterior regions. Supporting rings of metal, adapted to fit the contour of the sclera have been used as temporary supporting structures during surgery on the globe. However, none of these known devices have been used for surgical treatment of presbyopia, and none have been adapted to the special needs of prosthetic devices used in treating presbyopia.

A scleral band adapted to be fastened to the sclera of the eye in the region of the ciliary body in order to expand the sclera in that region and thereby increase the working distance of the ciliary muscle is described in applicant's U.S. Pat. No. 5,354,311, the entire disclosure of which is incorporated herein by reference. The scleral band of that patent is manufactured as a single unitary device that is placed on the surface of the sclera and fastened thereto, e.g., by suturing. Although the band is effective, alternate designs are possible that permit greater flexibility in installing the scleral band.

Accordingly, a need has continued to exist for a method of treating presbyopia that will increase the amplitude of accommodation of the presbyopic eye, thereby lessening or eliminating the need for auxiliary spectacle lenses to relieve the problems of presbyopia.

2. BRIEF DESCRIPTION OF THE PRIOR ART

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye, near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary body, a muscular ring of tissue, located just within the outer supporting structure of the eye, the sclera. The ciliary muscle is relaxed in the unaccommodated eye and therefore assumes its largest diameter. According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision of distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract, causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings and/or segments have been used in ocular surgery for various purposes. Rings and/or segments of flexible and/or elastic material, attached or prepared in situ by fastening the ends of strips of the material around the posterior portion of the globe, posterior to the pars plana (over the underlying retina), have been used to compress the sclera in certain posterior regions. Supporting rings of metal, adapted to fit the contour of the sclera have been used as temporary supporting structures during surgery on the globe. However, none of these known devices has been used for surgical treatment of presbyopia, and none has been adapted to the special needs of prosthetic devices used in treating presbyopia.

A scleral band adapted to be fastened to the sclera of the eye in the region of the ciliary body in order to expand the sclera in that region and thereby increase the working distance of the ciliary muscle is described in applicant's U.S. Pat. No. 5,354,331, the entire disclosure of which is incorporated herein by reference. The scleral band of that patent is manufactured as a single unitary device that is placed on the surface of the sclera and fastened thereto, e.g., by suturing. Although the band is effective, alternative designs are possible that permit greater flexibility in installing the scleral band.

Accordingly, a need has continued to exist for a scleral band for treating presbyopia and other eye disorders that allows the surgeon the opportunity of other methods of installing or implanting the band.

SUMMARY

A method of treating presbyopia and other eye disorders has now been found which comprises increasing the effective working distance of the ciliary muscle in the presbyopic eye.

Accordingly, it is an object of the invention to provide a method for treating presbyopia.

A further object is to provide a method for treating presbyopia by increasing the effective working distance of the ciliary muscle in the presbyopic eye.

A further object is to provide a method for treating presbyopia by increasing the radial distance between the equator of the crystalline lens and the ciliary body.

A further object is to provide a method of treating presbyopia by weakening the sclera in the region of the ciliary body.

A further object is to provide a treatment for hyperopia.

A further object of the invention is to provide a treatment for primary open angle glaucoma.

A further object is to provide a treatment for ocular hypertension.

A further object is to provide a method for increasing the amplitude of accommodation of the eye.

Further objects of the invention will become apparent from the description of the invention which follows.

DETAILED DESCRIPTION

Figure 1:
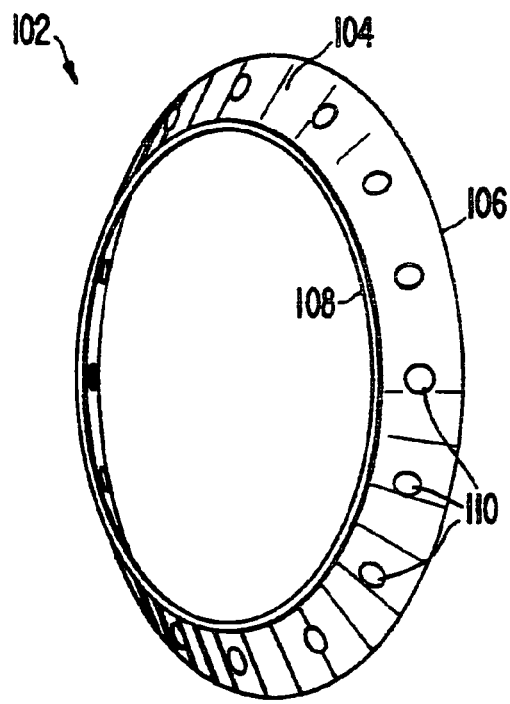
FIG. 1 shows an isometric view of a scleral expansion band of this invention.
Figure 2:
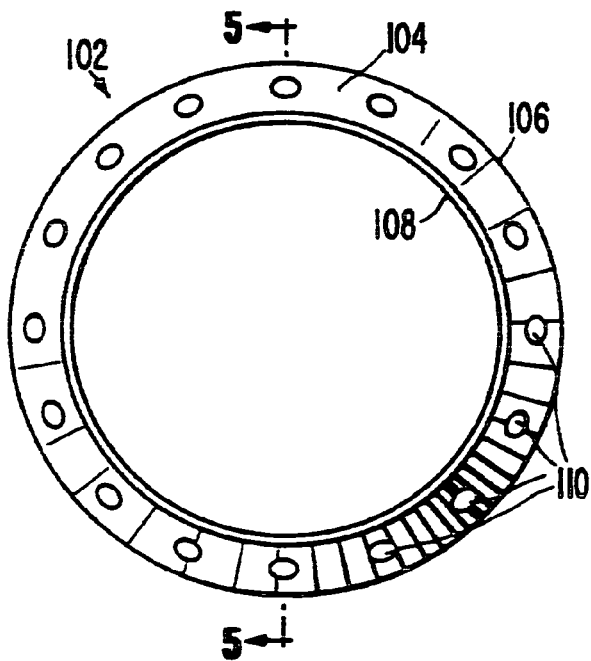
FIG. 2 shows an anterior elevational view of the band of FIG. 1.
Figure 3:
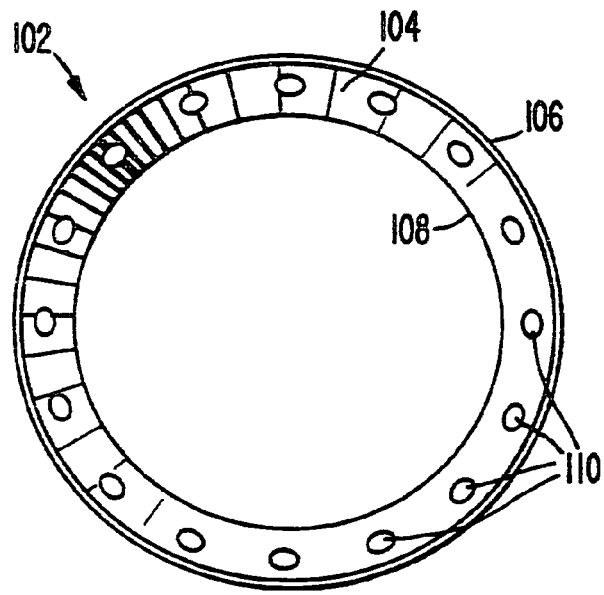
FIG. 3 shows a posterior elevational view of the band of FIG. 1.
Figure 4:
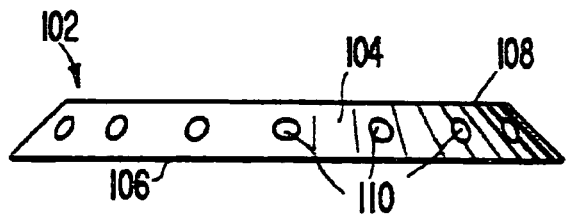
FIG. 4 shows a side view of the band of FIG. 1.
Figure 5:
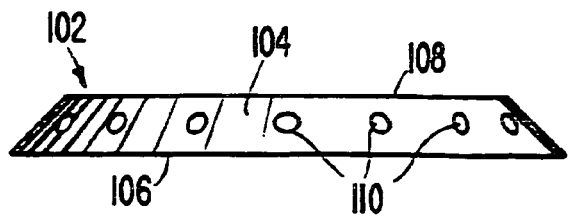
FIG. 5 shows a lateral sectional view of the band of FIG. 2.

This invention is based on a theory of presbyopia different from the classical theory of Helmholtz. Although the scope of the invention is not to be bound or limited by the inventor's theory, it is the inventor's view that the presbyopic loss of accommodation is due to decreased working distance of the ciliary muscle. This theory is described in more detail in U.S. Pat. No. 5,354,331, referenced above and incorporated herein by reference. Consequently, according to the invention, presbyopia is treated by increasing the effective working distance of the ciliary muscle. This is accomplished by increasing the distance between the ciliary muscle and the lens equator by increasing the diameter of the sclera in the region of the ciliary body.

This invention is based on a theory of presbyopia, developed by the inventor, regarding the cause of the loss of amplitude of accommodation that constitutes presbyopia. According to this view, accommodation in the non-presbyopic eye is not due to relaxation of the lens and capsule when the zonular tension is relaxed as a result of the contraction of the ciliary body. On the contrary, the contraction of the ciliary body, exerts a tension on the zonular fibers that in turn actually results in an increase in the equatorial diameter of the lens. However, the increased zonular tension causes a decrease in the peripheral volume of the lens that in turn results in a corresponding increase in the central volume of the lens. These regional volume changes in the lens are responsible for the change in optical power of the lens. This view differs from all previous theories of the mechanism of accommodation and its loss in presbyopia, in particular from Tscherning's theory which required the vitreous and attributed presbyopia to an enlargement of the nucleus of the lens. From the inventor's point of view, the difference between the change in the central anterior radius of curvature and the change in the central posterior radius of curvature which occurs in accommodation is explained by the force distribution generated by the zonular attachment to the lens and is not dependent on the topographical thickness of the elastic capsule of the lens, the vitreous, or pressure changes which occur between the anterior and posterior chambers, explanations which have been proposed in the prior art. According to the theory of this invention, presbyopia results when the distance between the ciliary body and the equator of the lens and its capsule becomes less with age as a result of the normal growth of the lens. The lens, being of ectodermal origin, continues to grow throughout life, albeit slowly. The rate of increase of the equatorial diameter is approximately 0.02 millimeters per year. On the other hand, the dimensions of the scleral shell of the eye, which is of mesodermal origin, do not increase significantly after about age 13 in a normally emmetropic, hyperopic or myopic eye. Consequently, the radial distance between the equator of the lens and capsule and the ciliary body, i.e., the distance measured perpendicularly to the optical axis in the plane of the ciliary body, decreases throughout life. It is well known in muscle physiology that as the length of the effective range of pull of a muscle, i.e., its effective working distance, is reduced, its effective force is reduced in a linear fashion. Since the distance between the ciliary body and the lens equator is decreasing throughout life, it is to be expected according to the theory of the invention that there would be a corresponding linear decrease in the amplitude of accommodation, as observed (Alpern, M., in The Eye, H. Dayson, Ed., Academic Press, New York, 1969, pp. 237-238), which would lead eventually to presbyopia.

According to the invention presbyopia is treated by increasing the effective working distance of the ciliary muscle. A number of procedures are available to the surgeon which can accomplish this increase in effective working distance.

A straightforward method of increasing the effective working distance of the ciliary muscle is to increase the distance between the equator of the crystalline lens and the inner diameter of the ciliary body in the presbyopic eye. This increased distance restores, at least to some extent, the distance through which the muscles of the ciliary body can contract, and thereby restores their ability to exert force on the lens and change its shape to accomplish accommodation. Any method that increases the radial distance between the lens and the ciliary body is effective in the method of this invention.

The effective working distance of the ciliary muscle can also be increased by shortening the zonules that connect the ciliary muscle to the equator of the crystalline lens. Similarly, procedures that shorten the body of the ciliary muscle itself or move its insertions in the scleral spur and the choroid can be employed to increase the effective working distance of the muscle. Finally, procedures that arrest the growth of the lens can stop the steady loss of amplitude of accommodation, and such procedures are considered as fully within the scope of this invention.

It is preferred to increase the lens-ciliary body radial distance by increasing the diameter of the sclera in the region of the ciliary body. Any method that can accomplish such an increase in the diameter of the sclera is considered to fall within the scope of the invention.

A preferred method of increasing the diameter of the sclera in the region of the ciliary body is to fasten to the sclera in that region a relatively rigid band having a diameter slightly larger than the section of the globe of the eye in the region of the ciliary body. In this way the sclera in that region is stretched and expanded so that the diameter of the circle describing the intersection of the plane of the ciliary body with the sclera is slightly increased. The ciliary body, located immediately inside the globe and attached to the sclera in this expanded region is thereby also increased in diameter.

Thus, the scleral expansion band of the invention adapted for fastening to the sclera of a human eyeball in the region of the ciliary body comprises an anterior rim and a posterior rim, the anterior rim being sized to lie adjacent to the anterior portion of a segment of the sclera of the human eyeball overlying the ciliary body of the eyeball and the posterior rim being sized to lie adjacent the posterior portion of the scleral segment, and rigid structural means extending between the rims and spacing said rims apart so that the anterior rim will lie outside the anterior portion of the scleral segment when the posterior rim lies outside the posterior portion of said scleral segment. The anterior rim, the posterior rim and/or the rigid structural means connecting the rims has a diameter greater than the exterior diameter of the scleral segment adjacent thereto.

Thus, the scleral expansion band of the invention is adapted to be fitted to the sclera of the globe in the region of the ciliary body. The band will have, at least in part, a diameter slightly greater than that of the sclera at the location where it is to be attached. When the band is fitted to the sclera and firmly attached thereto it will exert a radially outward tension on the sclera which expands the sclera and the underlying ciliary body. The scleral expansion band of the invention may be fastened to the sclera by any conventional surgical method. For example, the band may be a smooth solid band and be sutured to the sclera with sutures passing around the body of the band. A preferred band of the invention is provided with suturing holes through which the sutures may be passed. The band may also be fastened with conventional surgical staples or clips as are well known in the ocular surgery art. The band may be provided with projections or cut-out portions that can be used as anchoring points for sutures. The band may also be provided with projecting pins or the like which are inserted into or under the sclera to position the band and exert the appropriate radially outward tension. These pins may extend in an anterior and/or a posterior direction from the band, and may project from one or both rims of the band or from the web portion connecting the rims. The pins may also project in a generally tangential direction from the rims or the inside of the web and be provided with sharpened tips or the like whereby they will penetrate the sclera when the band is rotated and cause the sclera to be firmly fixed to the band and expanded. The band may also be adhesively fastened to the sclera with any physiologically acceptable surgical adhesive. A preferred surgical adhesive is a surgical grade cyanoacrylate adhesive. Mussel adhesive protein may also be used as a suitable adhesive.

A preferred embodiment of the scleral expansion band of the invention is illustrated in FIGS. 1-5. The band 102 has a low frustoconical shape and has a posterior rim 106 and an anterior rim 108, with a web 104 extending between the rims. The band may be provided with one or more holes 110 to assist in suturing the band to the sclera. The anterior rim 106 and the posterior rim 108 are both of generally circular shape. The taper in the diameter of the band is preferably selected in an individual case to fit the globe in the region of the ciliary body. Accordingly, a preferred band has a low frustoconical having a circular base about 20 millimeters in diameter. The radial thickness of the band will be determined by the rigidity required in the band and the strength of the material from which it is made. Typically the radial thickness of the band will be about 0.1 to 0.75 millimeters depending on the rigidity of the substance used to make the band. The diameter of the anterior rim 106 of the band will be determined by the size of the globe in the patient to be treated. Accordingly, different sizes of band are available wherein the lesser diameter ranges from about 14.5 millimeters to about 18.0 millimeters in 0.25 millimeter increments. The axial width of the band will typically be about 2 millimeters.

Figure 6:
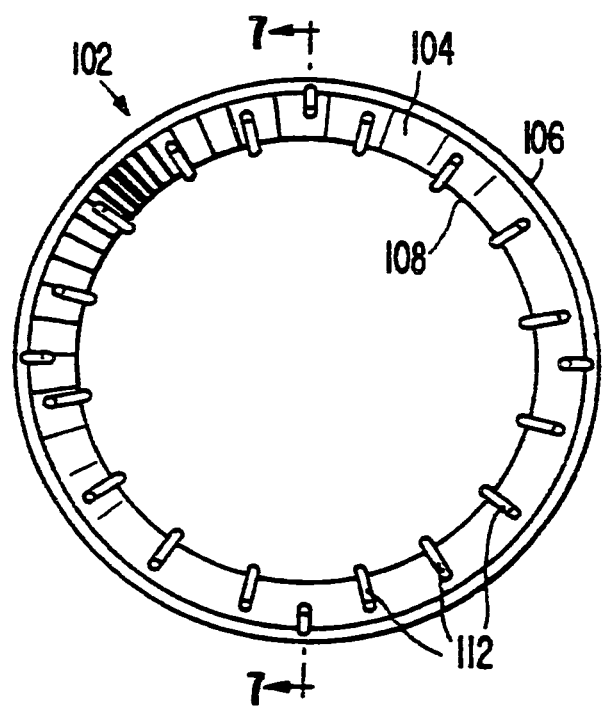
FIG. 6 shows a posterior elevation view of another embodiment of the scleral expansion band of the invention which uses pins for fixation.
Figure 7:
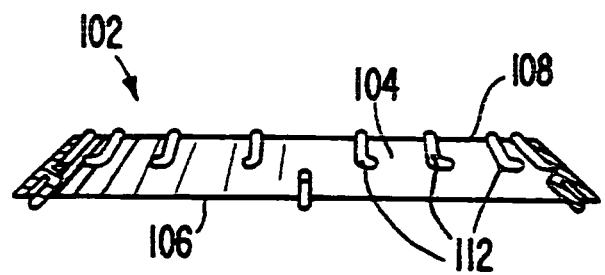
FIG. 7 shows a lateral sectional view of the band of FIG. 6.

An alternate embodiment of the scleral expansion band of the invention adapted to be fixed to the sclera by pins is illustrated in FIGS. 6 and 7. In this embodiment posterior pins 112 are fixed to the band and extend therefrom in a posterior direction while anterior pins 114 extend in an anterior direction.

Figure 8:
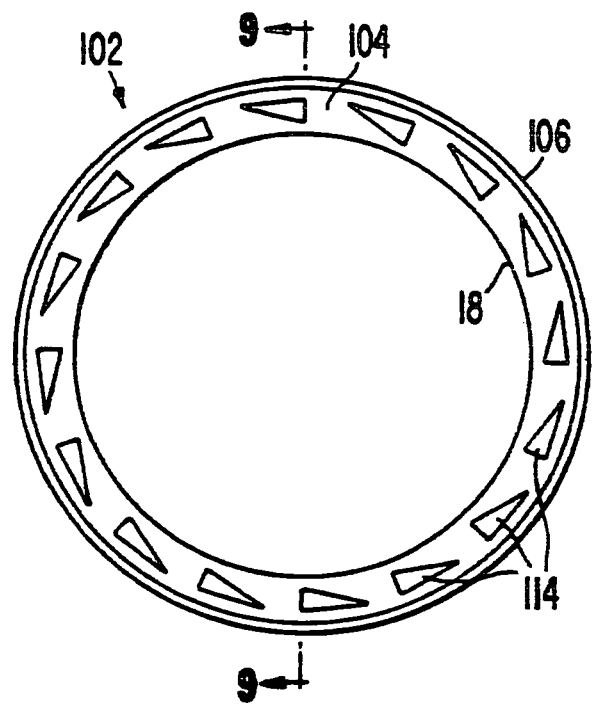
FIG. 8 shows a posterior elevation view of another embodiment of the scleral expansion band of the invention which uses tangentially extending fixation pins.
Figure 9:
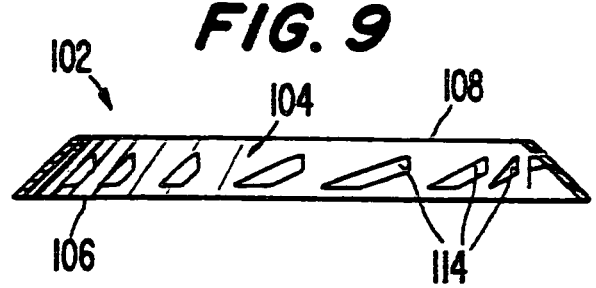
FIG. 9 shows a lateral sectional view of the band of FIG. 8.

Another embodiment of the band of the invention using interior tangentially-directed pins 114 is illustrated in FIGS. 8 and 9. This embodiment can be easily installed by placing it in position on the globe and rotating it to cause the tangential pins to penetrate the sclera and fasten it firmly to the band. This embodiment can be easily removed at a later time by merely rotating it in the opposite direction to withdraw the pins from the sclera.

The scleral expansion band of the invention is made of a material that is sufficiently rigid to exert a force on the sclera sufficient to produce the radial expansion required by the method of the invention and that is physiologically acceptable for long-term implantation or contact with the ocular tissues. Such materials are well-known in the surgical art and include suitable metals, ceramics, and synthetic resins. Suitable metals include titanium, gold, platinum, stainless steel, tantalum and various surgically acceptable alloys, and the like. Suitable ceramics may include crystalline and vitreous materials such as porcelain, alumina, silica, silicon carbide, high-strength glasses and the like. Suitable synthetic resins include physiologically inert materials such as poly(methyl methacrylate), polyethylene, polypropylene, poly(tetrafluoroethylene), silicone resins and the like. The band may also be made of composite materials incorporating a synthetic resin or other matrix reinforced with fibers of high strength material such as glass fibers, boron fibers, carbon fibers, alumina fibers or the like. Thus, the band may be made of glass-fiber-reinforced epoxy resin, carbon fiber reinforced epoxy resin, carbon fiber reinforced carbon (carbon-carbon), or the like. A preferred material is surgical grade poly(methyl methacrylate).

The scleral expansion band of the invention may be manufactured by any conventional technique appropriate to the material used, such as machining, injection molding, heat molding and the like.

The scleral expansion band may also be made in a plurality of parts that can be assembled prior to use or may be installed separately to form a complete band. The band may be adjustable in circumference. For example the band may be formed from a strip of material, e.g., metal or synthetic resin, with overlapping ends so that the ends may slide past one another thereby adjusting the circumference of the band. The length of the overlap may be adjusted, for example, by means of a tangential screw mechanism to adjust the circumference of the band and thereby the amount by which the sclera is expanded.

In practicing the method of the invention, the surgeon locates the proper region of the sclera to be expanded by measuring a distance of 1.5 millimeters posterior of the limbus. At this point the diameter of the circle of sclera surrounding the ciliary body is carefully measured and a band is selected having a minor diameter about 0.5 millimeter greater than the measured diameter. A circular incision is made through the conjunctiva completely around the globe at the selected region and the conjunctiva and Tenon's capsule are reflected to expose the substance of the sclera. For greatest accuracy in positioning the scleral expansion band, the diameter of the sclera as exposed by the reflection of the conjunctiva and Tenon's capsule is measured at a point 1.5 mm posterior to the limbus. Alternatively the size of sclera can be measured before the conjunctiva is incised. The band is then placed on the surface of the globe and sutured thereto preferably with interrupted stitches as conventional in ophthalmological surgery. In order to facilitate suturing the band to the sclera, the band may be perforated with holes. For example, a total of sixteen holes may be placed equidistant around the band.

It is also possible to expand the sclera in the region of the ciliary body by positioning a band within or just inside the sclera, the band having a diameter just greater than the natural diameter of the overlying tissue. In this way the interior band will expand the overlying tissue and produce the desired result of increasing the effective working distance of the ciliary muscle.

Other methods for increasing the diameter of the sclera in the region of the ciliary body may also be used in the treatment of presbyopia according to the invention. The sclera itself is a tough strong capsule comprised largely of collagen and held in a rigid state of tension by the internal ocular pressure (IOP). If the sclera is weakened in the area adjacent to the ciliary body, the IOP will cause that portion of the sclera to bulge outward, thereby increasing the diameter of the ciliary body and increasing the distance of the ciliary body from the lens. Any method of weakening the structure of the sclera is suitable. For example enzymatic degradation of the collagen by collagenase may be employed. The collagenase may be carefully injected in to the appropriate region of the sclera or may be applied topically. Equivalent enzymes or other chemical treatments that weaken the collagen of the sclera can also be used. Certain antimitotic drugs such as mitomycin are known to cause a softening of the sclera (scleromalacia), and these drugs can be applied to the region of the sclera adjacent to the ciliary body, either topically or by injection, to effect the desired weakening of the sclera. Other antimitotic pharmaceutical agents, e.g., methotrexate, azaribine, 6-mercaptopurine, 5-fluorouracil, daunorubicin, doxorubicin, cytarabine, the vinca alkaloids and the like, can also be applied to the sclera to weaken it and permit it to be expanded by the intraocular pressure.

Alternatively, the sclera in the region of the ciliary body may be weakened by surgical means. The sclera may be thinned or weakened by the surgical removal of a portion of its collagenous substance, as, for example by ablating a portion of the thickness of the sclera. This thinning can be accomplished by paring or by abrading the surface or by ablating the surface with laser irradiation. The sclera can also be weakened by incisions carefully placed at appropriate angles in the region overlying the ciliary body. The diameter of the sclera overlying the ciliary body can also be increased by making a complete periglobular incision and grafting into the incision appropriate tissue and/or physiologically acceptable structural material to increase the dimensions of the sclera. Thus an artificial scleral alloplant made of purified human collagen may be engrafted into such an incision. Other known biocompatible materials, e.g., poly(ethylene terephthalate), that are conventionally used in the construction of prosthetic devices may also be used for engrafting into such an incision. It is also possible to excise a small strip of sclera from the region overlying the ciliary body and replace it with a scleral alloplant as described above to provide an appropriate increase in the diameter of this region.

Alternatively the sclera in the region overlying the ciliary body can be weakened by irradiation with a laser beam to decompose partially the collagen fibers. Suitable lasers include those conventionally used in ocular surgery such as carbon dioxide lasers, helium-neon lasers, helium-cadmium lasers, argon ion lasers, krypton ion lasers, xenon lasers, nitrous oxide lasers, iodine lasers, holmium doped yttrium-aluminum garnet (YAG) lasers, excimer lasers, chemical lasers, harmonically oscillated lasers, dye lasers, nitrogen lasers, neodymium lasers, erbium lasers, ruby lasers, titanium-sapphire lasers, diode lasers and the like. Any irradiative treatment with ionizing or non-ionizing radiation that weakens the sclera may be used. For example irradiation with electrons, protons, or x-rays and the like, or irradiation with ultrasonic waves or the like can be used. Thermal burning and/or scarring in the appropriate area may also be used to induce an enlargement of the sclera in the area adjacent to the ciliary body.

Treatments designed to weaken the sclera in the region overlying the ciliary body can also be combined with application of the scleral expansion band of the invention. For example, the sclera can be treated with collagenase, mitomycin, or other antimitotic agent, as described above and the scleral band subsequently applied and fastened to the sclera. The band itself, its components and/or the sutures may also be coated or impregnated with the sclera-weakening agents whereby they can come into contact with the sclera and exercise their effect when the band is applied. In some cases the band may be later removed to leave the patient with a suitably expanded sclera.

Just as the distance between the ciliary body and the equator of the lens can be increased by expanding the sclera and ciliary body, the distance can be maintained and the progress of presbyopia arrested by stopping the growth of the crystalline lens. While such a treatment cannot reverse the course of presbyopia, it can arrest the progress of the symptoms, and is appropriate for treatment of patients in whom the presbyopia has not progressed very far. The growth of the lens can be arrested by administration of pharmaceutical compounds which stop cell division and growth. For example, colchicine can be administered to prevent cell division, thereby stopping the growth of the lens. Conventional antimitotic drugs may also be used to arrest the growth of the lens. Such drugs are well known and include, for example, methotrexate, azaribine, 6-mercaptopurine, 5-fluorouracil, daunorubicin, doxorubicin, cytarabine, the vinca alkaloids and the like. Such drugs may be applied topically or by injection into the appropriate structure of the eye where they will come into contact with the lens and exercise their pharmacological activity. If the drugs are sufficiently free of side effects, they may also be administered systemically, either by mouth or parenterally. The growth of the lens may also be arrested by physical treatments directed at the newly forming cells in the epithelium of the lens, particularly in the equatorial region of the lens. Treatments that prevent further division of the cells are appropriate for preventing further lens growth. Thus, the epithelial cells may be heated by laser radiation or ultrasonic irradiation, or inactivated by laser irradiation with a laser capable of directly disrupting chemical bonds within the structures of the cells. Sharply focused laser beams or irradiation with microscopic diode lasers positioned close to the equator of the lens are suitable for applying this radiation. Irradiation with electrons, protons, x-rays or the like may also be used to stop the further division of the epithelial cells of the lens. These treatments should be directed only to the portion of the lens structures that are composed of cells capable of dividing and should not be directed toward the substance of the lens where they might provoke the formation of cataracts.

Surgical methods that work more directly on the ciliary muscle may also be used to increase the effective working distance of the muscle. The body of the muscle itself may be shortened, for example by scarring induced by irradiation with suitable laser beams or beams of ionizing or non-ionizing radiation such as ultrasound or electron or proton beams or x-rays. The effective working range of the muscle may also be increased by moving its insertions to increase the distance between them. The ciliary muscle is inserted anteriorly into the scleral spur and posteriorly into the choroid. Treatment of either of these insertions to cause them to move apart from the complementary insertion will increase the effective working range of the ciliary muscle and improve the amplitude of accommodation according to the invention. Selective scarring of adjacent tissue planned to cause retraction of either insertion of the ciliary muscle is effective to accomplish this result. The scarring can be accomplished by thermal or radiative treatment of the tissue by the means and methods generally outlined above.

The methods of the invention which increase the amplitude of accommodation may also be of benefit in treatment of hyperopia in certain patients. Some youthful hyperopes can achieve relatively normal vision by compensating for their hyperopia through the natural accommodative ability of the eye. However, as this ability declines with age, they find that it becomes more difficult to attain normal vision by this process, and they begin to experience headaches and other symptoms, even at an age somewhat less than usual for the onset of presbyopia. Evidently, increasing the amplitude of accommodation by the method of this invention would be useful in restoring the ability of these patients to compensate for their hyperopia.

The method of this invention also has utility in the treatment of primary open-angle glaucoma, which shows a correlation with age in certain individuals. It has been found that, in general, IOP exhibits a linear increase with increasing age. (Armaly, M. F., On the distribution of applanation pressure I. Statistical features and the effect of age, sex, and family history of glaucoma, Archives of Ophthalmology, Vol. 73, pp. 11-18 (1965).) Among the general population is found a group of individuals who develop abnormally high intraocular pressures as a result of primary open angle glaucoma, a disease which is one of the most prevalent causes of blindness in the world. According to the theory of this invention, the linear increase in IOP with age is a direct result of the decrease in distance between the lens equator and the ciliary muscle and the resulting linear decrease in the effective pull of the ciliary muscle. Since the ciliary muscle inserts into the trabecular meshwork, the decrease in pull will decrease the size of the trabeculum and/or the drainage pores and result in a linear increase of intraocular pressure with age. In this view, the patients who develop primary open angle glaucoma may have a congenital predilection to narrower pores and/or smaller trabecular meshwork, so that when the ability of the ciliary muscle to exert force declines, after the age of 40 or thereabouts, they tend to develop excessively elevated IOP.

The method of the invention which increases the effective working distance of the ciliary muscle, and thereby increases the force that it can exert when it contracts, restores the level of force which the ciliary muscle exerts on the trabecular meshwork to a value characteristic of a more youthful eye. In this way it is expected that the tendency of an eye that is disposed to develop primary open angle glaucoma as it ages would be overcome and the onset of this disease would be prevented or at least postponed.

The ability of the ciliary muscle to exert tension on the lens by means of the zonules can also be increased by shortening the zonules, a procedure which increases the effective working range of the ciliary muscle. This shortening can be produced by heating the zonules by ultrasonic irradiation or laser irradiation. The zonules may also be treated with electrons, protons, x-rays and the like which may cause changes in the structure of the zonules resulting in shortening. The shortening of the zonules may also be brought about by application of chemical compounds that act to cause a shrinkage of the collagenous zonules.

The invention will be illustrated by the following examples which are intended for illustration only and are not to be interpreted as limiting the claims.

Example 1

This example illustrates the feasibility of increasing the diameter of the ciliary body by suturing an external band to the sclera.

Human cadaver eyes were selected for experimentation. The diameter of the sclera was measured using a shadow graph at distances of 1.5 millimeters and 3.5 millimeters from the limbus. The diameters were found to be 16.2 mm and 20 mm respectively. Bands were made from medical grade poly (methyl methacrylate) having a low frustoconical shape and a radial thickness of 0.5 mm. The internal diameter of the larger (posterior) side was 20 mm, and the smaller (anterior) diameters varied from 14.5 mm to 18.0 mm in 0.25 mm steps. A band was selected having a major diameter of 20 mm and a minor diameter of 18.0 mm. The band was placed on the sclera of a human cadaver eye so that the 18.0 mm diameter end of the band was 1.5 mm from the limbus and the 20 mm diameter end was 3.5 mm from the limbus. The band was sutured through the holes with 16 interrupted 6-0 polyester (Mersilene, Ethicon, Inc.) stitches to the sclera. This resulted in a clearly observable stretching of the sclera in the region of the ciliary body. The pupil became dilated by about 1.5 mm. Since the iris inserts into the ciliary body, the pupillary dilation demonstrated that the induced scleral stretching was also moving the ciliary body outward, thereby increasing its diameter and its distance from the equator of the lens.

Example 2

This example illustrates the treatment of presbyopia in patients.

Following informed consent, six presbyopic patients with otherwise normal eyes, except for minimal refractive errors, had scleral expansion bands of the invention sutured to the sclera in the region of the ciliary body. Their age ranged from 47 to 60 years, there were three males and three females, and their preoperative amplitude of accommodation varied from 1.3 to 2.7 diopters. The ophthalmological examination including biomicroscopy was normal. Following local infiltration into the conjunctive with prilocalne HCl for injection (Citanast (Astra), 40 mg/ml), a 360 degree limbal based peritomy was performed and the sclera was cleaned of Tenon's capsule. Using vernier calipers, a distance of 1.5 mm posterior to the limbus was measured from the limbus and the scleral diameter was measured at that location. A band of the type made in Example 1 was selected having a minor diameter of from 0.5 mm to 1.5 mm greater than the measured diameter of the sclera. The band was sutured to the sclera with 16 interrupted 6-0 polyester (Mersilene, Ethicon, Inc.) stitches. The patients were given antibiotic-steroid drops to use for five days. Postoperatively, the patients were followed daily for five days and then weekly. The results are presented in Table 1 below.

TABLE 1

Preoperative and Postoperative Amplitude of Accommodation

| Patient No. | Age (yr) | Sex | Preoperative | | Postoperative | |
|---|---|---|---|---|---|---|
| | | | Near Point (cm) | Amplitude of Accommodation (diopters) | Near Point (cm) | Amplitude of Accommodation (diopters) |
| 1 | 55 | M | 75 | 1.3 | 9 | 11.1 |
| 2 | 50 | F | 45 | 2.2 | 10 | 10.0 |
| 3 | 47 | F | 37 | 2.7 | 16 | 6.25 |
| 4 | 56 | M | 56 | 1.7 | 9 | 11.1 |
| 5 | 60 | F | 38 | 2.6 | 12 | 8.3 |
| 6 | 46 | M | 40 | 2.5 | 17 | 5.8 |

Figure 10:
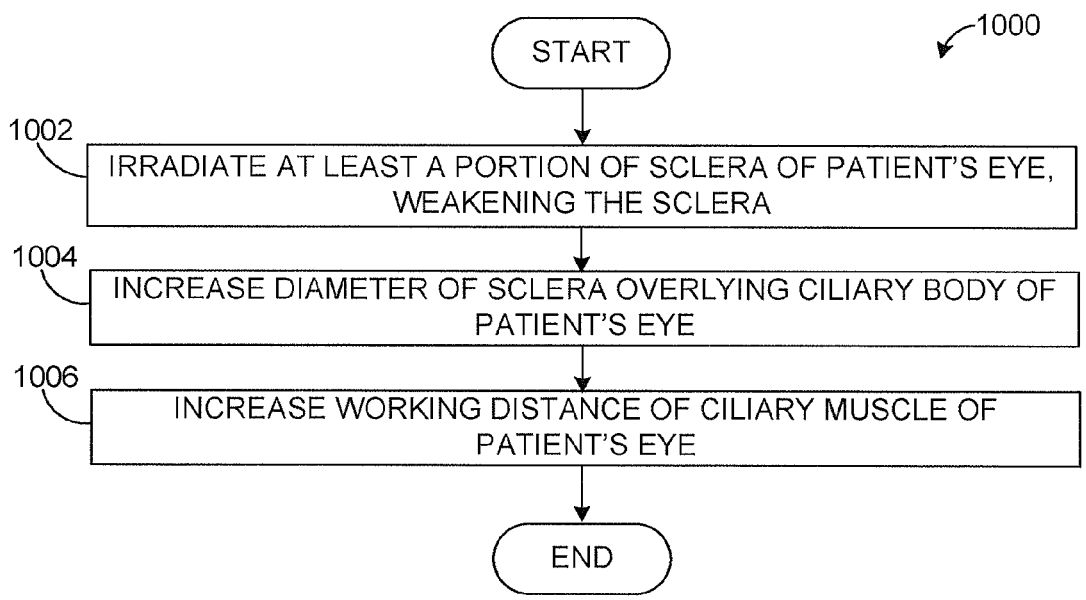
FIG. 10 shows a method for treating presbyopia and other eye disorders.

FIG. 10 shows a method for treating presbyopia and other eye disorders. As shown in FIG. 10, at least a portion of the sclera in a patient's eye is irradiated, thereby weakening the sclera, at step 1002. The diameter of the sclera overlying the ciliary body of the patient's eye is increased at step 1004. The working distance of the ciliary muscle of the patient's eye is increased at step 1006. During this process, the thickness of the sclera in the region of the ciliary body of the eye is reduced without forming an opening completely through the sclera.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A method, comprising:

increasing a diameter of a sclera overlying a ciliary body of an eye as a function of irradiating at least a portion of the sclera;

wherein increasing the diameter of the sclera comprises reducing a thickness of the sclera in a region of the ciliary body without forming an opening completely through the sclera;

wherein increasing the diameter of the sclera increases a working distance of a ciliary muscle of the eye.

2. A method, comprising:

weakening a sclera of an eye using laser irradiation to increase a diameter of the sclera overlying a ciliary body of the eye;

wherein weakening the sclera comprises reducing a thickness of the sclera in a region of the ciliary body without forming an opening completely through the sclera;

wherein weakening the sclera increases a working distance of a ciliary muscle of the eye.

3. A method, comprising:

irradiating at least a portion of a sclera of an eye to increase a diameter of the sclera overlying a ciliary body of the eye;

wherein irradiating at least the portion of the sclera comprises reducing a thickness of the sclera in a region of the ciliary body without forming an opening completely through the sclera;

wherein irradiating at least the portion of the sclera increases a working distance of a ciliary muscle of the eye.

\* \* \* \* \*

UNITED STATES PATENT AND TRADEMARK OFFICE
CERTIFICATE OF CORRECTION

| | | |
|---|---|---|
| PATENT NO. | : 8,663,205 B2 | Page 1 of 1 |
| APPLICATION NO. | : 11/322728 | |
| DATED | : March 4, 2014 | |
| INVENTOR(S) | : Schachar | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1487 days.

Signed and Sealed this
Second Day of June, 2015

Michelle K. Lee
*Director of the United States Patent and Trademark Office*